United States Patent [19]

LaForge et al.

[11] 4,143,661
[45] Mar. 13, 1979

[54] POWER SUPPLY FOR BODY IMPLANT AND METHOD FOR OPERATION

[75] Inventors: David H. LaForge, Kensington; Peer M. Portner, Berkeley, both of Calif.

[73] Assignee: Andros Incorporated, Berkeley, Calif.

[21] Appl. No.: 859,914

[22] Filed: Dec. 12, 1977

[51] Int. Cl.² ............................................. A61N 1/00
[52] U.S. Cl. .................................. 128/419 R; 3/1.7; 128/1 D; 128/2.1 A; 128/419 PS
[58] Field of Search ..................... 3/1.1, 1.7; 128/1 D, 128/2.1 A, 419 C, 419 E, 419 PG, 419 PS, 419 R

[56] References Cited

U.S. PATENT DOCUMENTS

| | | | |
|---|---|---|---|
| 3,824,129 | 7/1974 | Fagan, Jr. | 128/419 PS |
| 3,942,535 | 3/1976 | Schulman | 128/419 PS |

OTHER PUBLICATIONS

Senning, "Journal of Thoracic & Cardiovascular Surgery", vol. 38, No. 5, Nov. 1959, p. 639.

Primary Examiner—Wm. E. Kamm
Attorney, Agent, or Firm—Fitch, Even, Tabin & Luedeka

[57] ABSTRACT

A power supply system to operate an implanted electric-powered device such as a blood pump. A secondary coil having a biocompatible covering is implanted to subcutaneously encircle either the abdomen or the thigh at a location close to the exterior skin. The secondary coil is electrically interconnected with an implanted storage battery and the blood pump. A primary coil of overlapping width is worn by the patient at a location radially outward of the secondary coil. An external battery plus an inverter circuit in a pack is attached to a belt having a detachable buckle connector which is conventionally worn about the waist. Efficient magnetic coupling is achieved through the use of two air-core windings of relatively large diameter.

12 Claims, 5 Drawing Figures

POWER SUPPLY FOR BODY IMPLANT AND METHOD FOR OPERATION

This invention relates to electric power supplies and more particularly to a power supply for a device which is implanted within a living body and a method for operation thereof.

The relatively high amount of power required by circulatory support devices, such as a partial or total artificial heart, has rendered most implantable, self-sufficient energy sources inapplicable, such as those used for a pacemaker. Only high-power, radioisotope heat sources have held any promise of sustained outputs of several watts; however, the utilization of such an energy source has been complicated by its inherent need for a miniature, high efficiency heat engine, as well as by serious radiation-related problems. All other practical approaches to powering an artificial heart or circulatory assist system of some type necessarily depend on a more or less continuous flow of energy from outside the body. Results of early efforts at infection-free maintenance of long-term percutaneous connections were discouraging and thus highlighted the desirability, at least for the long term, of powering such an implanted device though intact skin.

One of the earliest approaches to the transmission of energy across intact skin involves the generation of a radio frequency field extending over a substantial area of the body, such that significant power could be extracted from coils located in the vicinity of the implanted power-consuming device itself. Placement of substantial amounts of ferrite materials within such coils to permit the capture of a greater proportion of the incident field was also investigated, as reported in the article by J. C. Schuder et al. in the 1964 Transactions ACEMB. However, difficulty has been experienced in reconciling the conflicting requirement of magnetic circuit geometry with a surgically feasible, variable tissue structure. In another proposed alternative design, a secondary coil is implanted in such a manner that the center of the coil remains accessible through a surgically constructed tunnel of skin; however, such devices have not yielded satisfactory performance. Predominant failure modes included necrosis of the skin tunnel tissue caused by mechanical pressure and excess heat generation — see the 1975 report of I.I.T. Research Institute, by Brueschke et al., N.I.H. Report No. NO1-HT-9-2125-3, page 25.

As a result of the present invention, it has been found that a satisfactory system can be achieved by the employment of a secondary coil which is implanted just below the skin of the abdomen or the thigh so that it encircles the body member along most of its length and lies at a location close to the skin. The system includes an implanted storage battery plus the necessary interconnections between the secondary coil, the battery and the electric-powered device, which will likely be a circulatory assist device of some type. A primary coil, in the form of an encircling belt which is greater in width than the secondary implanted coil, fits around the body member in the region just radially outward thereof. A portable external A.C. power source, usually a rechargeable battery plus an appropriate inverter, is in electrical connection with the primary coil. These coils function efficiently as an air-core transformer and sufficient power is transcutaneously supplied via the secondary coil to both operate the device and charge the implanted storage battery.

Objectives and features of the invention will be apparent from the following detailed description of a preferred embodiment thereof, when read in conjunction with the accompanying drawings wherein.

Figure 1:
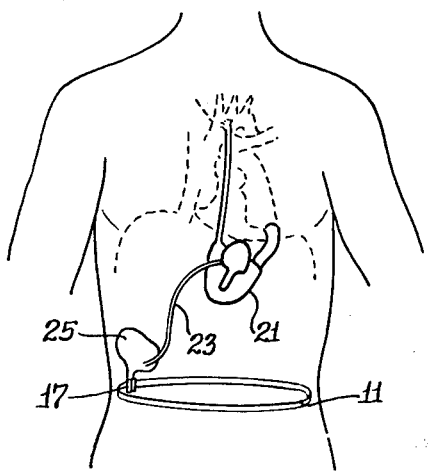
FIG. 1 is a diagrammatic depiction of the implanted portion of a power supply system shown in conjunction with a circulatory blood pump within a living human.
Figure 3:
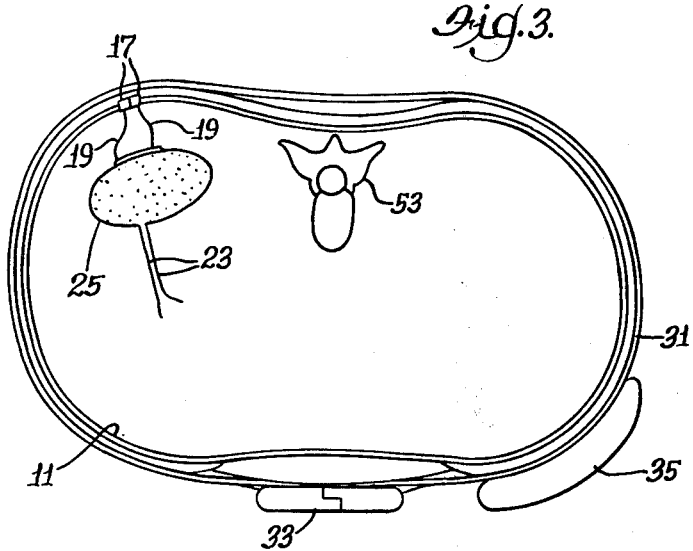
FIG. 3 is a diagrammatic sectional view looking vertically downward through the body of the wearer.

Illustrated in FIG. 1 is a portion of a human body wherein a secondary coil in the form of a strip 11 has been implanted to encircle the abdomen in the region of the waist. The secondary coil 11 takes the general shape of a broad ellipse which approaches circularity, and it exhibits only a minor reduction in open circuit inductance relative to a perfectly circular coil. As best seen in FIG. 3, the strip 11 which constitutes the secondary coil is implanted close to the surface of the skin for nearly its entire length, and the thickness of the tissue overlying the implanted secondary coil 11 should be about 5 millimeters.

Figure 4:
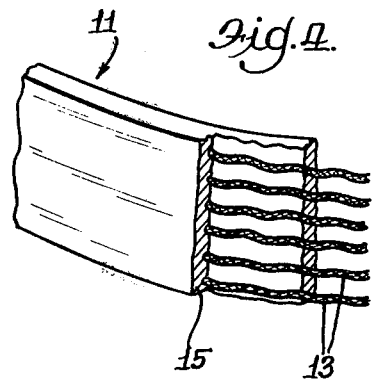
FIG. 4 is an enlarged fragmentary perspective view showing a preferred construction of an implantable secondary coil, such as that diagrammatically depicted in FIG. 1.

The strip 11 may be made from a plurality of generally parallel electrical conductors 13 which are appropriately disposed in an outer biocompatible jacket 15. As best seen in FIG. 4, the conductors 13 are made by braiding multiple strands of copper alloy wire and are formed in a sinuous or wavy shape to further increase flexibility and to also provide an inherent capability for stretching in the longitudinal direction. Although six conductors 13 are shown in FIG. 4, it should be understood that the strip 11 which constitutes the secondary coil may include as few or as many conductors as necessary to provide the desired number of turns. For example a single turn coil may be satisfactory although a step-up transformer may be needed to provide the necessary voltage at practical frequencies.

The strip 11 is preferably made by suitable embedding, as by an extrusion or molding process, the sinuous conductors 13 within a suitable synthetic rubber or elastomer, such as that sold under the trademark Silastic. This arrangement provides some degree of stretch plus adequate flexibility to cope with normal body movements. If desired, the exterior surface of the strip 11 can be coated with an appropriate coating material that will improve its biocompatibility, as is generally known in the art relating to prosthetic devices.

The length of the strip 11 is proportioned to fit the body of the patient, and of course the length will be about twice as long if the secondary coil is implanted about the abdomen than if it were to be implanted about the thigh. The width and thickness of the strip 11 of course determine the number of conductors 13 that can be included therewithin, and generally it is felt that the strip should not be more than about 2 centimeters wide. In this respect, it is believed that an adequate secondary coil can be provided by a strip 11 only about 1 centimeter wide. The thickness of the strip need not be greater than about 3 millimeters, and it is considered that an acceptable secondary coil can be provided using a strip 11 having a radial thickness of only about 1.5 mm.

Suitable connectors 17 are provided at both ends of the strip 11 which join the conductors 13 serially in end-to-end connection to provide a continuous coil having a number of turns equal to the number of conductors. These multicircuit connectors 17 may be of any suitable design, for example, pin and socket, which can be easily mated and then locked together and sealed after the strip 11 has been implanted in the body of the patient. Attached to each of the mating connectors 17 will be a lead 19 for carrying power from the secondary coil to the remainder of the system.

Figure 2:
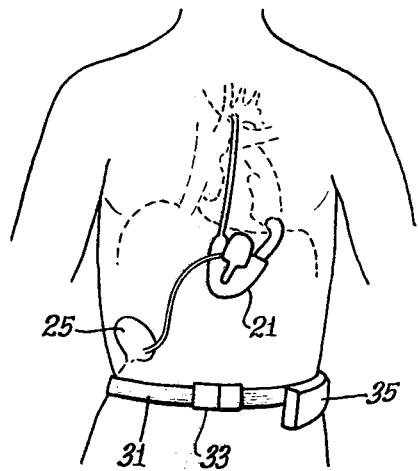
FIG. 2 is a view similar to FIG. 1 showing the wearer with the primary coil belt and battery in place.

Depicted in FIGS. 1 and 2 is a blood pump in the form of a left ventricular assist device 21 that will usually operate on D.C. power, e.g., on a solenoid-type principle. The leads 19 from the mating connectors 17 and a pair of electrical leads 23 from the blood pump 21 are directed to an implanted module 25 that includes not only the electronic rectifying and control components, but also a storage battery 27. The storage battery 27 allows the system to function independently of any outside power source for a minimum period of time, for example, 45 minutes, and thus permits detachment of the external power to permit bathing or swimming or the like.

The system is powered and charged via coupling to a primary coil which is constituted by an outer belt 31 having a disconnectable buckle 33. When the secondary coil 11 is implanted in the abdomen about the waist, the primary coil can be fashioned to take the place of an ordinary belt which would be worn about the waist with a skirt or a pair of trousers. To assure maximum efficiency, it is important that the primary coil overlaps the secondary coil, and realizing that there will be some shifting of the exterior belt 31 during wearing, the exterior belt is designed to be substantially wider than the implanted strip 11. Generally, the exterior belt 31 will not be more than about 5 centimeters in width, and it is considered that a belt width of about 4 centimeters should be adequate. Because the belt 31 will be worn exterior of the body, there is no real limitation on its thickness; however, it is considered that a thickness of about 4 mm. shoud be adequate.

Because the belt may thus have a fairly large cross-sectional area, the conductors 35 in the exterior belt 31, which when joined serially end-to-end create the primary winding, may be No. 12 aluminum wire. Preferably, twice as many turns of aluminum wire are used in the primary coil compared to the number of turns in the implanted secondary coil. For example, there may be 14 turns in the primary coil and 7 turns in the secondary coil, and the implanted electrical device may be designed to operate on 12 volts. The buckle connector 33 includes two halves which latch together, and each of the halves would include 14 mating points of connection, such as a pin and socket arrangement, to connect the 14 parallel conductors 35 serially end-to-end to create a continuous coil of 14 turns.

Preferably, all 14 of the turns can be connected at the buckle 33, and the two ends of the primary coil are located intermediate the ends of the belt where a pack 35 including a rechargeable battery plus an inverter circuit is connected thereto. With this arrangement, a direct connection to the battery-inverter 35 can be made, without the need for additional leads, to apply A.C. power to the primary winding. Alternatively, the two terminals could be connected through the buckle connector 33 to a pair of leads which are electrically connected to the battery pack that is suitably carried on the belt, as depicted. The material from which the exterior belt 31 is made is not particularly critical inasmuch as it might only be in contact with the exterior surface of the skin, and when the secondary coil is implanted around the abdomen, it may be worn outside of one's clothing. Thus, the aluminum conductors 35 might, for example, likewise be embedded in a flexible polymeric material which might be faced with a outer leather layer to give the resemblance of a conventional dress belt.

Figure 5:
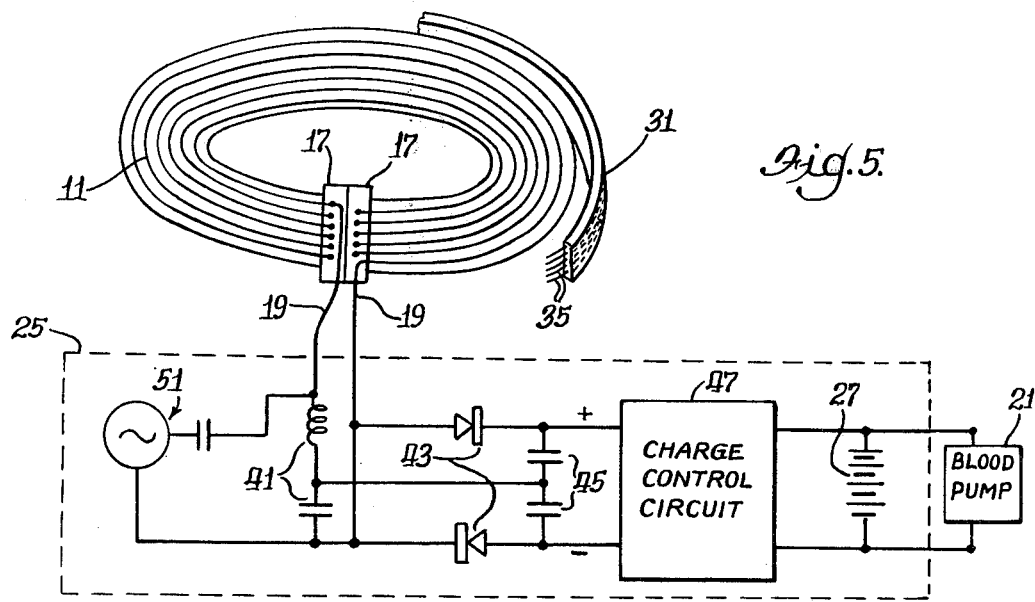
FIG. 5 is a schematic view of the power supply system showing exemplary portions of an electronic control arrangement that might be used.

As diagrammatically depicted in FIG. 5, the electronic control package preferably includes appropriate low-pass filters 41 ahead of the rectifier circuits 43 to make sure that accidental interception of large electromagnetic fields does not cause damage to the implanted electronic components. However, very high frequency radiation or even microwave radiation should not present any serious difficulty because the longitudinal self-inductance of the relatively narrow secondary band should present sufficient impedance, by itself, to prevent a serious build-up of currents at such higher frequencies. The induced A.C. voltage in the secondary coil 11 is applied to rectifier circuits 43 and voltage-doubler capacitors 45 before it reaches cicuitry 47 which controls the charge that will be applied to the standby D.C. battery 27 and regulates the power that will be passed to the blood circulation device 21. The standby battery 27 will be designed to operate at 8–16V. and likely at 12V. Such D.C. voltage at the battery 27 can be provided using 14 turns in the primary coil and a 100 kHz square wave with about 7 turns in the air-core secondary coil.

While the air-core secondary coil 11 does not radiate significantly at its intended operating power frequencies, it nevertheless can be made to serve as a convenient loop antenna for the transmission of the data generated within a living body, for example, by the blood assist circulation device 21, to an exterior receiver (not shown). A low-power telemetry transmitter system 51 can be provided which will use the secondary coil 11 as a loop transmitting antenna. In this manner, telemetered information can be received in the reverse direction on the primary coil 31, or by a direct reception with a remotely located radio receiver (now shown).

The illustrated circumabdominal site for the strip 11 which constitutes the secondary coil is preferred because it is ideally suited to interface with a primary coil belt 31 worn about the waist. Three small, vertically directed incisions will provide sufficient access to permit implantation of the strip 11 to be readily accomplished. A suitably-shaped trocar, which might for example be curved with a flattened cross-section, would be directed from one incision to the next defining a tunnel passageway. The secondary strip 11 would be suitably clamped to the trailing end of the trocar and then drawn into place by the withdrawal of the instrument. Three such threading operations would complete the entire implantation of the secondary coil.

Although the belt is preferably implanted dorsal to the spinal column 53 as illustrated in FIG. 3, it could be passed ventral to the spine (although this would admittedly entail a more complicated threading procedure) so that is would follow the path generally shown in dotted outline in FIG. 3. Although this detour would result in some degradation in the coupling coeffcient that will be accomplished between the primary and secondary coils, the secondary coil would still remain adjacent the skin throughout the major portion of its length, and the reduction in the coupling coefficient should be only about five or six percent.

Because of the relatively large diameter (i.e., at least about 15 to 25 cm.) of the two air-core coils a very high magnetic coupling coefficient is achieved in an overall lightweight iron-free system. Although the invention has been described with regard to certain preferred embodiments, it shoud be understood that various changes and modifications such as would be obvious to one having the ordinary skill in this art may be made without departing from the scope of the invention which is defined solely by the claims appended hereto. Various of the features of the invention are set forth in the claims which follow.

What is claimed is:

1. A power supply system for an electric-powered device which is implanted within a living body, which system comprises a secondary coil in the form of at least one turn of electrically conductive wire disposed within a biocompatible outer covering, which coil is of a size and configuration for subcutaneously encircling a major member of the living body, said coil further being of a size and configuration for location close to the exterior skin along at least a major portion of the length of said coil, a storage battery adapted for implantation within the living body, means for electrically interconnecting said secondary coil and said storage battery, and means for connecting said storage battery to the electric-powered device for supplying energy thereto, a primary coil in the form of an encircling belt having a width greater than the width of said secondary coil and being proportioned to fit around the exterior of the major member in radial alignment with said secondary coil, and an external power source in electrical connection with said primary coil which is operable to transcutaneously supply sufficient power, via said primary and secondary coils, to charge said implanted storage battery for operation of said implanted device.

2. A power supply system in accordance with claim 1 wherein said secondary coil is in the form of a strip which has a thickness not greater than about 3 mm. and the ends of which are joined together.

3. A power supply system in accordance with claim 2 wherein said secondary coil strip comprises metal conductors spaced apart from one another and embedded within flexible polymeric material.

4. A power supply system in accordance with claim 3 wherein said strip is not greater than about 2 cm. wide.

5. A power supply system in accordance with claim 1 wherein said secondary coil is formed from a plurality of individual conductors the ends of which are serially connected to one another at a multicircuit connector which joins the ends of said strip into said encircling coil.

6. A power supply system in accordance with claim 5 wherein said conductors are braided strands of wire formed in a sinuous pattern which are embedded in an elastomeric material to allow stretch in a longitudinal direction.

7. A power supply system in accordance with claim 1 wherein said primary coil belt includes a buckle which electrically serially connects the ends of a plurality of individual conductor lengths into a continuous multi-turn coil and wherein said external power source a battery-inverter combination is supported by attachment to said belt.

8. A power supply system in accordance with claim 1 wherein telemetry means are adapted to be implanted and connected to said secondary coil which serves as an antenna for the transmission of data generated within the living body.

9. A method of powering an electric-operated blood circulation device which is implanted within a living body, which method comprises implanting a storage battery within the living body and connecting said storage battery to the blood circulation device, implanting a secondary coil so that it subcutaneously encircles a major member of the living body at a location close to the exterior skin, electrically connecting said implanted coil to said implanted storage battery, surrounding said air-core secondary coil with a primary coil of a greater width which circumscribes said major member of the living body so that said primary and secondary coils are aligned, and applying sufficient A.C. power to said primary coil to provide a flux that transcutaneously reaches said secondary coil and induces sufficient A.C. voltage in said secondary coil to charge said implanted storage battery.

10. A method in accordance with claim 9 wherein said secondary coil is disposed within about 5 mm. of the skin throughout the major portion of its length.

11. A method in accordance with claim 10 wherein said coil is disposed ventral to the spine.

12. A method in accordance with claim 10 wherein said coil is disposed dorsal to the spine.

* * * * *